(12) United States Patent
Kitson et al.

(10) Patent No.: US 6,824,785 B1
(45) Date of Patent: Nov. 30, 2004

(54) SKIN TREATMENT COMPOSITION AND METHODS OF USE

(76) Inventors: C. Neil Kitson, 3414 W. King Edward Ave., Vancouver, BC (CA), V6S 1M3; Jenifer L. Thewalt, 3670 Trinity St., Vancouver, B.C. (CA), V5A 1S6

( * ) Notice: Subject to any disclaimer, the term of this patent is extended or adjusted under 35 U.S.C. 154(b) by 318 days.

(21) Appl. No.: 09/780,060

(22) Filed: Feb. 9, 2001

Related U.S. Application Data
(60) Provisional application No. 60/181,374, filed on Feb. 9, 2000.

(51) Int. Cl.$^7$ .............................. A61K 7/00; A61K 9/00; A61K 9/127
(52) U.S. Cl. ....................... 424/401; 424/400; 424/450; 514/937; 514/944
(58) Field of Search ................................ 424/400, 401, 424/450; 514/937, 944

(56) References Cited

U.S. PATENT DOCUMENTS

| | | |
|---|---|---|
| 5,643,899 A | 7/1997 | Elias et al. |
| 5,720,963 A | 2/1998 | Smith |
| 5,916,578 A * | 6/1999 | Kawada et al. .............. 424/401 |

FOREIGN PATENT DOCUMENTS

WO    WO-90/01323 A1 *  2/1990

OTHER PUBLICATIONS

"Concise Encyclopedia Chemistry", p. 599, 1994.*
Abraham, et al.; "Investigation of Membrane Structure and Dynamics by Deuterium NMR: Application to the Stratum Corneum" in Mechanisms of Transdermal Drug Delivery; Potts and Guy, eds.; 1997; pp163–198.
Wertz, et al; "Covalently Bound Lipids of Human Stratum Corneum"; J. Invest Dermatol 92:109–111, 1989; pp109–111.
Imokawa, et al.; Importance of intercellular lipids in water-retention properties of the stratum corneum: induction and recovery study of surfactant dry skin; Arch Dermatol Res (1989) 281:45–51.
Abraham, et al.; "Fusion Patterns of Liposomes Formed from Stratum Corneum Lipids"; J. Invest Dermatol 90:259–262; 1988.
Pilgram, et al.; "Electron Diffraction Provides New Information on Human Stratum Corneum Lipid Organization Studied in Relation to Depth and Temperature" J Invest Dermatol 113:403–409, 1999.
Kitson, et al.; "A Model Membrane Approach to the Epidermal Permeability Barrier"; American Chemical Society, 1994; pp 6707–6715.
Imokawa, et al.; "Selective Recovery of Deranged Water-Holding Properties by Stratum Corneum Lipids"; The Society for Investigative Dermatology, Inc. 1986; pp758–761.
Wertz, et al.; "Essential Fatty Acids and Epidermal Integrity", Arch Dermatol—vol. 123, Oct. 1987; pp1381–1384.
Bouwstra, et al.; "A Model Membrane Approach to the Epidermal Permeability Barrier: An X–ray Diffraction Study"; Biochemistry 1997; 7717–7725.

Imokawa; "Stratum Corneum Lipids Serve as a Bound–Water Modulator"; The Society for Investigative Dermatology, Inc. 1991; pp 845–851.
Man, et al; Exogenous Lipids Influence Permeability Barrier Recovery in Acetone–Treated Murine Skin; Arch Dermatol—vol. 129, Jun. 1993, pp 728–738.
Thewalt, et al., Models of Stratum Corneum Intercellular Membranes: The Sphingolipid Headgroup is a Determinant of Phase Behavior in Mixed Lipid Dispersions; Biochemical and Biophysical Research Communications, vol. 188, No. 3, 1992, pp 1247–1252.
Proksch, et al.; "Barrier Function Regulates Epidermal DNA Synthesis", The Journal of Clinical Investigation, Inc., vol. 87, May 1991, 1668–1673.
Schurer, et al., "The Biochemistry and Function af Stratum Corneum Lipids"; Advances in Lipid Research, vol. 24, pp 27–56; 1991.
Elias, et al.; "Structural and Lipid Biochemical Correlates of the Epidermal Permeability Barrier"; Advances in Lipid Research, vol. 24, pp. 1–26, 1991.
Abraham, et al.; "Interaction between corneocytes and stratum corneum lipid liposomes in vitro"; Elsevier Science Publishers B.V. (Biomedical Division) 1990, pp 119–125.
Abraham, et al.; "Effect of epidermal acylglucosylceramides and acylceramides on the morphology of liposomes prepared from stratum corneum lipids"; Biochimica et Biophysica Acta 939 (1988) 403–408.
Ansari, et al.; "Fatty Acid Composition of the Living Layer and Stratum Corneum Lipids of Human Sole Skin Epidermis"; Lipids, vol. 5, No. 10, pp 838–845, 1970.
Wertz, et al.; "Hydroxyacid Derivatives in Human Epidermis"; Lipids. vol. 23, No. 5 (1988).
Cullis, et al.; "The Bilayer Stabilizing Role of Sphingomyelin in the Presence of Cholesterol"; Biochimica et Biophysica Acta, 597 (1980) 533–542.
Monash, et al.; "Location and Re–Formation of the Epithelial Barrier to Water Vapor"; A.M.A. Archives of Dermatology; vol. 73, Dec. 1958.

* cited by examiner

*Primary Examiner*—Gary Kunz
*Assistant Examiner*—Marina Lamm
(74) *Attorney, Agent, or Firm*—Oppendahl & Larson LLP

(57) ABSTRACT

A composition which when topically applied to the skin of a mammal reduces trans-epidermal water-loss and provides an improved epidermal barrier contains an aqueous dispersion of at least two lipids, preferably at least three lipids, in a non-crystalline phase lamellar array, preferably bilayer membranes in the form of liposomes. These lipids adopt a crystalline lamellar phase upon application to mammalian skin which resist washing with mild detergents and water. The composition can be formulated as a pharmaceutical preparation, and can be used in a method of recovering or otherwise improving a mammalian skin permeability barrier by administering the composition to the skin or hair and allowing the composition to dry. The dried composition adopts a crystalline lamellar phase after said administering to the skin. The composition thus provides a permeability barrier in cases where the natural barrier has been depleted, damaged or requires improvement. This barrier resists removal by detergent, solvent, or mechanical means over an extended period of time.

6 Claims, 5 Drawing Sheets

Figure 2: M1 of three lipid formulations across a wide physiological temperature range.

SKIN TREATMENT COMPOSITION AND METHODS OF USE

This application claims the benefit of U.S. Provisional Application No. 60/181,374 filed Feb. 9, 2000, which application is incorporated herein by reference.

BACKGROUND OF THE INVENTION

Many types of skin treatments have been developed which attempt to repair damaged skin. Typically, consumers and manufacturers evaluate these skin treatments on a subjective/objective basis based on whether the treatment relieves symptoms such as roughness, dryness, redness, or the discomfort of pain or itch. Some specific measures used to determine effectiveness are: feel (greasy/non-greasy), drying time, barrier effectiveness and duration, smell, efficacy of moisturization and the like. These features are determined by the lipids or hydrocarbons of the composition, other additives and the solvent in which they are provided.

Skin treatments typically come in the form of creams or lotions, which are emulsions of lipids and other components. Commercially successful skin treatments such as Vaseline™ petroleum jelly still have recognized draw-backs, such as their greasy feel, and the long drying time required. This prevents users from quickly applying the Vaseline™ and returning to other activities. These and other drawbacks affect existing skin treatments.

In recent years, it has been recognized that the permeability barrier of mammalian skin is found in unusual intercellular domains in the upper layers of the epidermis, and is composed mainly of three lipid classes: ceramide, cholesterol and free fatty acid. (see Kitson N, et al. A model membrane approach to the epidermal permeability barrier. Biochemistry. 1994;33:6707–15). To date no one has successfully applied this information to reconstitute this permeability barrier when it is lost. This is particularly relevant to humans who lose or damage this barrier either as the result of a pathological condition, or in the course of daily activities.

It is an object of the invention to provide a novel composition for use as a skin or hair treatment. It is also an object of the invention to take advantage of the phase transition properties of certain lipid formulations that result upon application to the skin, to provide an improved skin or hair treatment. It is a further object of this invention to provide formulations of therapeutic and bioactive agents in a treatment for use in topical skin-care applications.

SUMMARY OF THE INVENTION

The instant invention provides a composition which when topically applied to the skin of a mammal reduces trans-epidermal water-loss and provides an improved epidermal barrier. The composition comprises an aqueous dispersion of at least two lipids, preferably at least three lipids, in a non-crystalline phase lamellar array, preferably bilayer membranes in the form of liposomes. These lipids adopt a crystalline lamellar phase upon application to mammalian skin which resist washing with mild detergents and water.

In addition, the invention comprises a pharmaceutical preparation comprising a therapeutic compound in an aqueous formulation of at least two lipids in a non-crystalline phase lamellar array which adopt a crystalline lamellar phase upon application to mammalian skin and further comprising a therapeutic or bioactive agent.

The invention further comprises a method of recovering or otherwise improving a mammalian skin permeability barrier by administering to the skin or hair a composition of lipids comprising an aqueous formulation of at least two lipids in a non-crystalline phase lamellar array; and allowing said composition to dry, wherein said dried composition adopts a crystalline lamellar phase after said administering to the skin.

The perceived advantages of the invention are:
1. Provision of a permeability barrier in cases where the natural barrier has been depleted, damaged or requires improvement
2. Provision of a barrier that resists removal by detergent, solvent, or mechanical means.
3. Extended duration of efficacy.
4. Improved acceptability, particularly in feeling "non-greasy".
5. Can be a vehicle for a wide variety of active agents.
6. May allow reduced wastage of active agents.
7. May improve quality of skin or hair.

DETAILED DISCLOSURE OF THE INVENTION

Figure 1:
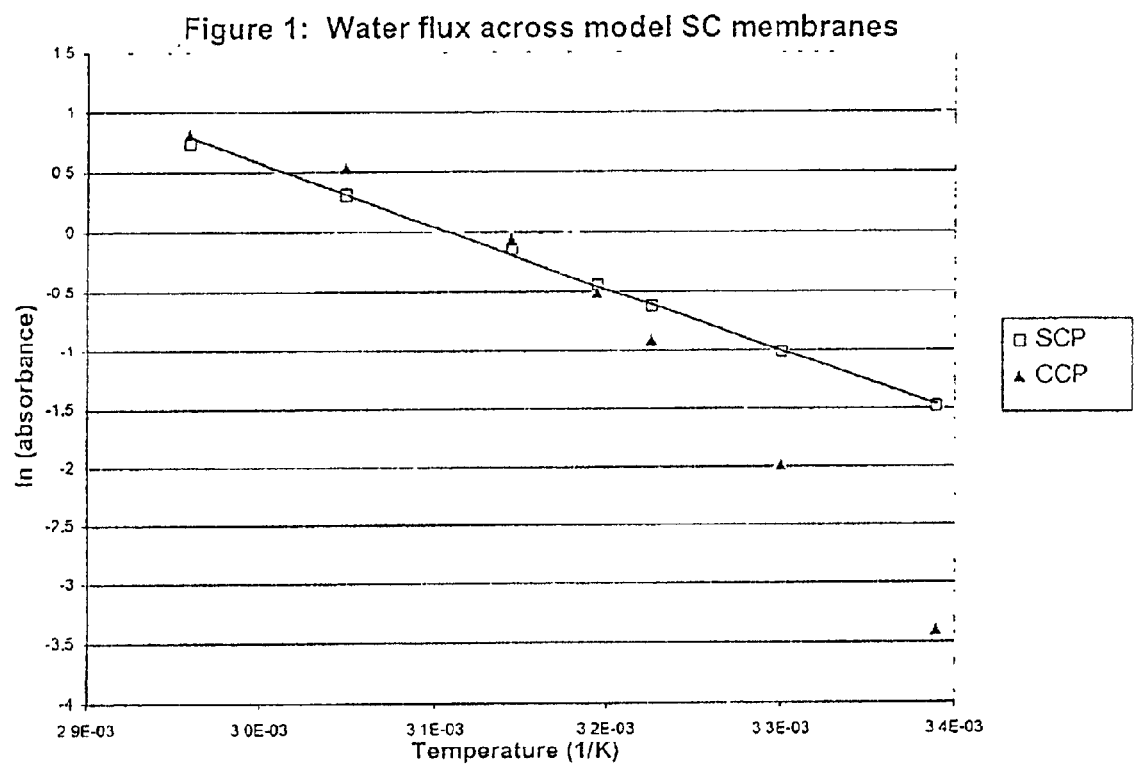
FIG. 1: Water flux across model SC membranes

The instant invention provides a composition which when topically applied to the skin of a mammal reduces trans-epidermal water-loss and provides an improved epidermal barrier. The composition comprises an aqueous dispersion of at least two lipids in a non-crystalline phase lamellar array, preferably bilayer membranes in the form of liposomes. These lipids adopt a crystalline lamellar phase upon application to mammalian skin. It is a fundamental discovery of this invention that only a limited group of lipids are capable of converting from non-crystalline to a crystalline phase upon skin application, and that this composition provides a superior skin treatment. The composition can also be used to provide protection to the skin against environmental irritants, or stress. It can also be used in combination with therapeutic or bioactive agents which are improved when combined in the skin treatment of the invention.

The composition of the invention includes lipids which undergo phase transition from a non-crystalline phase to a crystalline phase upon application to the skin.

The phase of a lipid formulation may be determined by a variety of analytical techniques. Such techniques are well known in the art and include NMR, X-ray diffraction, Fourier transform infrared spectroscopy, calorimetry assays, fluorescent probe techniques, ESR probes, biochemical assays and other methods. These techniques generally characterize the degree and type of mobility of lipids bound in a restricted physical array.

For the purposes of the instant invention, the phases discussed all relate to lipids which are capable of adopting lamellar arrays such as monolayers, bilayers, etc. Other phases are recognized for amorphous powders, or water-in-oil type phases (such as the hexagonal phase HI and HII) but are not relevant to the instant invention. Note also that lipids dissolved in an organic solvent, such as ethanol or propylene glycol/ethanol do not have a designated "phase" because they are individually solvated and have very little systematic organization.

A crystalline phase is defined as a physical state in which membrane lipids are organised on a lattice and have extremely reduced lateral and rotational mobility compared to the fluid arrangement of other mammalian cellular membranes. For example, in some crystalline phases, individual lipid molecules within the membrane show no diffusional or rotational motion on the deuterium NMR time scale, or are arranged in a rectangular lattice when examined by wide angle x-ray diffraction. For purposes of this invention, a crystalline phase formulation is defined where 70% or more of lipids by mass are in a crystalline phase.

Non-crystalline phases include liquid crystals ("$L_\alpha$"), gels ("$L_\beta$"), and other recognized non-crystalline phases such as the "liquid ordered" phase (Ipsen, J. H., G. Karlstrom, O. G. Mouritsen, H. W. Wennerstrom, and M. J. Zuckermann (1987) Phase equilibria in the phosphatidylcholine-cholesterol system. Biochim. Biophys. Acta. 905:162–172.) Liquid crystals possess the characteristics of both liquids and crystalline solids; they have some degree of order, but some degree of fluidity as well. These may be further characterized as smectic, nematic or other arrays. Gel phase refers to an array where the lipids are packed in a stiff, near-crystalline hexagonal array, having sharp spacing. A significant energy barrier lies between liquid crystal and gel phases. However, a further significant energy barrier lies between gel phase and a crystalline phase. For purposes of this invention a non-crystalline phase formulation is found where at least 70% of lipids by mass are in a non-crystalline phase.

A "complex phase" is a lamellar array that exhibits more than one phase. This is possibly caused by selected components of the mixture adopting one phase, while other components adopt an alternative phase. A complex phase bilayer may be stable, or it may dissociate into different sub-mixtures. Resolution of phases can be quite good in some membranes, and complex phases can be detected when only 1–5% by mass is in the alternative phase.

It is an important observation of this invention that crystalline phase transition upon application to the skin is restricted to certain limited mixtures of lipids. These mixtures can be defined in the negative. For example, a lipid composition capable of phase transition does not include significant amounts of phospholipids, apparently because of the effective size of the head group. As such, compositions of the invention do not include phosphatidylcholine, phosphatidyl-glycerol, or their family members. In particular, in many formulations, sphingomyelin will not permit phase transition. Additionally, because phase transition requires saturated acyl chains, significant amounts of unsaturated acyl chains will block crystalline phase formation. Fatty acids used must therefore be saturated; "essential" fatty acids (or unsaturated fatty acids), or surfactants, will prevent crystalline phase formation.

In this invention, the preferred embodiment employs a mixture of at least two lipids, and preferably three lipids, selected from among the following classes:

1. A non-swelling amphiphile with a relatively small effective head-group size such as a ceramide or a pseudo-ceramide. Non-polar examples such as diacylglycerol may be possible. Preferred ceramides may be of mixed chain length, and can be prepared semi-synthetically from sources such as egg-sphingomyelin, or milk or spingomonas ferment extract, and chemically converted or they may extracted from sources such as bovine brain. Synthetic or semi-synthetic compounds with the features of ceramides or pseudo-ceramides may also be useful. These include ceramide 1, ceramide 1A, ceramide 2, ceramide 3, cerammide 4, cerammide 5, ceramide 6 II, or Questamide H 2. A sterol which incorporates into a stable lamellar array, such as cholesterol. Other sterols may be used if they do not disrupt crystalline phase formation.

3. A fully saturated fatty acid, such as palmitic acid, or fatty alcohol, or the like. Any chain length or mixture of chain lengths may be employed, but 14C is the lowest thought to be stable in a lamellar array.

The preferred embodiment does not include detergents, surfactants, or unsaturated acyl chains which may prevent or reduce the phase transition. Preferred formulations are described in detail, below.

The phase transition significantly alters membrane physical properties. In particular, phase transition from non-crystalline to crystalline phase significantly reduces water permeability, although the relation is likely to be complex. The instant inventors have discovered that the water permeability barrier of skin which has been depleted of intercellular lipids can be successfully reconstituted by the lipid formulation of the invention which forms a crystalline phase lamellar arrangement upon application to the skin. The significance of the phase transition has not here-to-for been recognized.

Water permeability is a key function of the skin. The water permeability barrier has been traced to multiple layers of intercellular lipids in the deeper layers of the stratum corneum ("SC"). Delivery of the lipids in lamellar arrays into the SC before transition to the crystalline phase is an important achievement of the invention, because it provides for a superior skin treatment which will adequately replace depleted intercellular lipids.

The benefits of a skin barrier replacement composition can be assayed by a measure of Trans-Epidermal Water Loss (or TEWL). TEWL is described in the examples below. It generally encompasses water loss through skin sections that do not include sweat glands, or other features designed specifically to regulate water homeostasis.

Other important features of phase transition include the benefit that is harder to remove crystalline phase lipids from the skin by detergent, solvent or mechanical means, than non-crystalline lipids, or lipid formulations such as Vaseline™ petroleum jelly. Crystalline lipids can also alter pharmacokinetic profile of therapeutic or bioactive agents contained within formulations applied to the skin.

A preferred composition of the invention consists of a ceramide, a cholesterol and a saturated fatty acid in molar ratio of 1–5:1–5:1–5. The optimised ratio of lipids is selected to achieve a fully hydrated non-crystalline (liquid crystalline or gel phase) liposomal preparation which will form a crystalline array upon "application to the skin". The preferred molar ratio is about 1:1:1, but formulations with up to a five-fold excess of one lipid over any other are expected to be satisfactory.

The composition is administered to the skin as a liposome formulation in aqueous buffer, and may take the form of a liquid or semi-liquid cream or lotion. It is known that the typical intercellular lipid composition of ceramide, cholesterol and fatty acid has a consistency of solid candle wax when in place and crystallized. As such, it is difficult to formulate these lipids into a suitable product for application to the skin, if the lipids are not present in a non-crystalline phase. Moreover, it is important that these lipids are present in homogeneous formulations of liposomes, such that they do not phase separate after application to the skin.

The preferred composition comprises liposomes such as multi-lamellar vesicles (MLVs) and/or large unilamellar vesicles (LUVs). These liposomes are stabilized by suitable aqueous conditions, such as salt, pH and level of hydration. It is important to use aqueous buffers which are suitable for skin application, and have minimal salt concentrations to avoid complicating effects on drying. Low salt buffers (i.e. 1 mM), such as HEPES buffer at pH 7.4 and CHES at pH 9.0 are good examples. Generally pH 7.0–pH 10 is anticipated to be acceptable for the starting composition, with the lower limit set by the pKa of fatty acid in the membrane, and the upper limit set by cosmetic concerns, such as skin irritability of basic solutions. Using these parameters, other buffer solutions can be selected systematically.

It is possible that small amounts of organic solvents or ethanol may be in the buffer, such as residual amounts remaining from the manufacturing process. Such solvents are acceptable if they do not reduce the commercial desirability of the skin treatment, and if they do not interfere with the non-crystalline to crystalline phase transition.

Typically, an aqueous buffer for the invention would also include additives such as anti-microbial agents (e.g., Kathon™), preservatives and/or anti-oxidants, such as vitamin E. Amounts must be low enough to not result in skin irritation.

All formulations of the invention have preferred features of acceptable skin treatments, including look, smell, and feel. They are non-greasy and are quick drying, and have reduced requirements for re-application because of their extended duration of efficacy. They are not easily removed by detergent, solvent or mechanical means, and they provide an excellent skin-barrier replacement formulation.

Formulations of the invention are not limited for use with damaged skin only. In the broadest sense, they may be used in any condition for a skin or hair treatment, such as with dry skin or damaged hair. They have applications in the area of cosmetics, related to improved skin texture, delivery of ceramides to skin or hair, and improved hydration properties. Further, because the liposomes of the invention are unlikely to be washed off, they have particular application in protecting the skin from abrasive chemicals (hair care) or for workers who are exposed to water for long periods of time (Fish industry). Other foreseeable applications include vehicles to prevent colonization of skin by pathogenic bacteria (e.g., methicillinresistant *Staphylococcus aureus*), agents to reduce exposure to environmental pathogens such as poison ivy as well as "patches" of vehicles which, after drying, will be geographically fixed in place for the duration of application.

Examples below illustrate small-scale manufacturing and storage of the compositions. Other methods for small scale manufacturing are well known in the art. Large scale manufacturing and storage (on the 20–10,000 liter scale) can be achieved by scale up of the small scale methods or other procedures well known in the art.

Alternative preferred compositions of the invention are selected to have the same or similar activation energies of phase transition and similar phase behaviour. In alternative formulations, the users must be aware of effects of lipid classes (since these are believed to be the important determinants of phase behaviour), the effects of chain length modification; and the effect of substitution of cholesterol for cholesterol analogs.

"Application to the skin" as used in this specification, includes any mechanical means of application to an epidermal surface of a mammal. The mechanical means is preferably application by hand, but may include any other technique, including aerosol sprays, brushes, cloths, bandages, micro-sponges, patches, paints (some containing acrylics) and the like.

A particular advantage of the composition is the high fluid mobility of liposome particles. This is in distinct contrast to the candle wax consistency of crystalline phase lipid bilayers. Without being bound by any mechanism of action, it is hypothesized that upon application to the skin the aqueous liposome formulation will penetrate the upper layers of the stratum corneum ("SC"). The liposomes accumulate in spaces where natural skin lipids may have been removed by mechanical or chemical challenge or leaching; or where absent because of pathological condition, including skin or systemic disease.

Application to the skin results in a rapid series of changes to the composition, all or some of which are responsible for inducing the phase transition of the lamellar arrangement. These changes include pH change, drying, packing and pressure changes, ionic strength change, temperature change; fusion of liposomes in close proximity; all of these changes may influence hydration state of the composition. All or some of these changes drive conversion from the non-crystalline phase to the crystalline phase. The process proceeds rapidly (at approximately the speed that water evaporates from the skin), leaves little or no "oily" or unsatisfactory feel to skin, and provides a long lasting trans-epidermal water-loss barrier.

An additional benefit of the aqueous formulation of liposomes, compared to organic solvent or detergent formulations, is that pH and ionic strength of aqueous buffer can be carefully adjusted to provide the most preferred formulation for administration to the skin, and the preferred non-crystalline phase for the formulation before it is applied. The liposomes are therefore highly suited for penetration of the intercellular spaces.

Typically, the formulation is applied in liquid dosages of about 1–40 $\mu$l/cm2 skin, containing between 0.1–20% lipid by weight. This range is very flexible; useful amounts can range from a lower limit of 0.1 mg lipid/cm2 skin to a higher limit capped only by the ability of skin to absorb it. There is likely to be a range of preferred dosages, depending on the type of damage (or the extent of barrier recovery required) in the skin of the user, and method and frequency of application.

Formulations of the invention are well suited for use in hair and scalp treatment. They may, for example, protect hair fibers from drying or decay, or reduce the leaching of dye from the hair fiber. They may also facilitate the delivery of ceramides or other lipids to the hair fiber thus prooting hair quality. The formulation of the invention may also be used to reduce the percutaneous absorption of agents applied to hair, such that the toxicity is reduced.

The invention also encompasses the use of the phase-transition lipid composition in combination with a therapeutic or bioactive agent. Topical formulations of this kind provide a reliable method of administering agents with activity on the skin surface, in the epidermis, hair follicle, dermis, or activity elsewhere in the body after trans-epidermal delivery.

A wide variety of therapeutic or bioactive agents can be employed. Basically, any composition that can be incorporated into the lipid formulation of the invention at amounts that do not inhibit phase transition upon application to the skin is encompassed. This very large list includes anti-inflammatory agents, antibiotics, antivirals, antifungals, antihistamines, antipruritics, antineoplastic agents, carboxylic acid analogs, natural and synthetic vitamins and analogs, or artemisinin analogs, steroids, sunscreens, and skin agents such as retinoids.

Dosages and amounts of therapeutic or bioactive agents will have to be determined byclinical trials with predetermined therapeutic end-points, but all dosages should be selected based on known effective concentrations in the free form. The invention may allow the use of significantly lower doses of certain agents, because the crystalline lamellar phase will prevent wastage of these agents.

The following examples are illustrations of the composition and methods of the invention as claimed in the claims, and are not intended to limit the scope of those claims.

EXAMPLES

Bovine brain sphingomyelin, bovine brain ceramide-III (CER, or ceramide) and cholesterol (CHOL) were purchased from Sigma (St. Louis, Mo.) and used without further purification. The acyl chains of sphingomyelin and ceramide obtained from bovine brain were mainly stearic (C18:0), nervonic (C24:1) and lignoceric (24:0). Perdeuterated palmitic acid (PA-d31) (or 'hexadecanoic') acid was purchased from C/D/N Isotopes Inc., Pointe-Claire, Quebec.

Example 1

In this example, the lipid composition of the invention undergoes phase transition upon administration to a filter, modelling the effect of administration to the skin. This example demonstrates the surprising advantages of the CCP (ceramide:cholesterol:palmitic acid) composition of the invention over SCP (sphingomyelin:cholesterol: palmitic acid).

A Franz chamber (described generally in Bronaugh, R. L. Current issues in the In Vitro measurement of percutaneous absorption. In: Dermal Absorption and Toxicity Assessment. M. S. Roberts and K. A. Walters eds. Marcel Dekker, New York, 1998 pp 155–187) was adapted for measurement of water permeability through lipid dispersions by substituting model membranes prepared on Millipore filters for skin.

The lipid mixtures were prepared by adding the indicated lipids dissolved in an organic solvent (benzene: methanol 7:3) in desired molar ratios. When thoroughly mixed, solutions were lyophilized to remove the organic solvent. Lipid dispersions were prepared by hydrating the lyophilized mixture at 95° C. with $10^{-3}$ M CHES buffer, pH 9. The final lipid concentration was 8 mg/ml, and consisted of liposomes (MLVs). Five aliquots of 25 $\mu$l (total 1 mg lipid) were deposited onto a 9 mm diameter circle on a Millipore GS hydrophilic membrane having a 0.22 $\mu$m pore size. The solution was allowed to dry between aliquots, and finally the lipid-coated membrane was dried at 40° C. for at least one hour. The membranes were then sandwiched between Durapore GV type gaskets (7 mm diameter) and then between 7 mm diameter neoprene gaskets before mounting in the Franz chamber. The mounted membrane was exposed to water or a standard buffer (phosphate or HEPES at pH 7.4) at temperatures as indicated, on the lower side; and to dry nitrogen gas at room temperature on the upper side.

Water vapour emanating from the membrane was measured by Fourier Transform Infrared Spectroscopy. The FTIR instrument used was based on a Michelson interferometer with some modifications. Dry nitrogen gas was used to carry water vapour from the sample surface to the detector. This was achieved using two lengths of stiff polypropylene tubing (3 mm i.d.): one to carry dry nitrogen from a liquid nitrogen source to a brass fitting attached to the upper chamber of the Franz diffusion cell; the other to carry the nitrogen gas with water vapour from the sample surface to the detector. The sensitivity of the measurement was adjustable by varying the flow rate of the gas or changing the optical path length of the detector. Using our current methods, water fluxes of 1 g $m^{-2}$ $h^{-1}$ (on the order of 1 nmol $cm^{-2}$ $s^{-1}$) can be measured reproducibly.

After a 10 minute waiting time (to allow the level of water vapour in the nitrogen stream to equilibrate), an interferogram was recorded and Fourier transformed to a transmission intensity-energy spectrum. The transmission intensities were converted to absorbance intensity readings and the peak intensity level of the OH vibrational band at 3744 $cm^{-1}$ was converted to a water flux by comparison with the value determined for water saturated air at 0° C. Experiments involving temperature changes included a 30-minute temperature equilibration period prior to measurement.

The spectrometer was "purged" with dry nitrogen overnight to remove background water vapour from the gas lines and detector system. A Fourier transformed transmission intensity-energy (background) spectrum confirmed that very little water was present and a high signal to noise ratio was achieved. The background spectrum served as a reference for converting the Fourier transformed interferograms of water vapour measurements from a transmission (arbitrary intensity) to an absorbance spectrum. Absorbance intensities are linearly related to the water concentration in the nitrogen gas, and, with a known gas flow rate, to flux.

FIG. 1 shows the surprising and genuinely remarkable results of the invention, based on two determinations of the temperature dependence of water flux across different barriers in model membrane systems: SCP is sphingomyelin:cholesterol: palmitic acid (1:1:1) and CCP is ceramide:cholesterol:palmitic acid (1:1:1). The slope for CCP at higher temperatures appears to be indistinguishable from SCP, but is quite different below the "break point" in the curve, near 45° C. This temperature corresponds to the phase transition temperature (from crystalline to liquid crystalline membranes) that can be observed with NMR and x-ray diffraction in ceramide dispersions of similar composition (See Example 2 below and see Bouwstra JA, et al. A model membrane approach to the epidermal permeability barrier: an X-ray diffraction study. Biochemistry. 1997;36:7717–25; and Kitson N, et al. A model membrane approach to the epidermal permeability barrier. Biochemistry. 1994; 33: 6707–15.))

These results demonstrate, for the first time, that below the phase transition temperature, CCP provides a remarkably improved permeability barrier over SCP. These results also establish that crystalline membranes, even with random geometry, affect water flux. These results have not previously been observed.

Example 2

This example establishes by NMR the phase of three formulations under different conditions. The formulations are CCP in aqueous phase, (i.e. liposomes prior to administration on a filter); CCP after application to a filter; and SCP after application to a filter. The example confirms by NMR that across a wide physiological temperature range, aqueous CCP remains in liquid crystal phase. However, when applied to a filter, the same CCP formulation, adopts a crystalline phase. SCP retains a liquid crystalline phase on the filter.

Briefly, the lipids were dissolved in benzene/methanol (7:3 v/v) in amounts as indicated and freeze-dried. The palmitic acid component consisted of an equal parts perdeuterated palmitic acid (for an NMR marker). The powder was then hydrated at 95° C. in deuterium depleted water containing the same buffer as in Example 1 (CHES at pH 9). In order to achieve homogeneous dispersions, at least 5 freeze-thaw cycles took place between 95° C. and liquid nitrogen temperature.

CCP in aqueous phase was analysed directly by standard NMR techniques.

CCP and SCP applied to the filter was prepared as in Example 1: Five aliquots of 25 μl (total 1 mg lipid) were deposited onto a 9 mm diameter circle on a Millipore GS hydrophilic membrane having a 0.22 μm pore size. The solution was allowed to dry between aliquots, and the lipid-coated membrane was dried at 40° C. for at least one hour.

Figure 2:
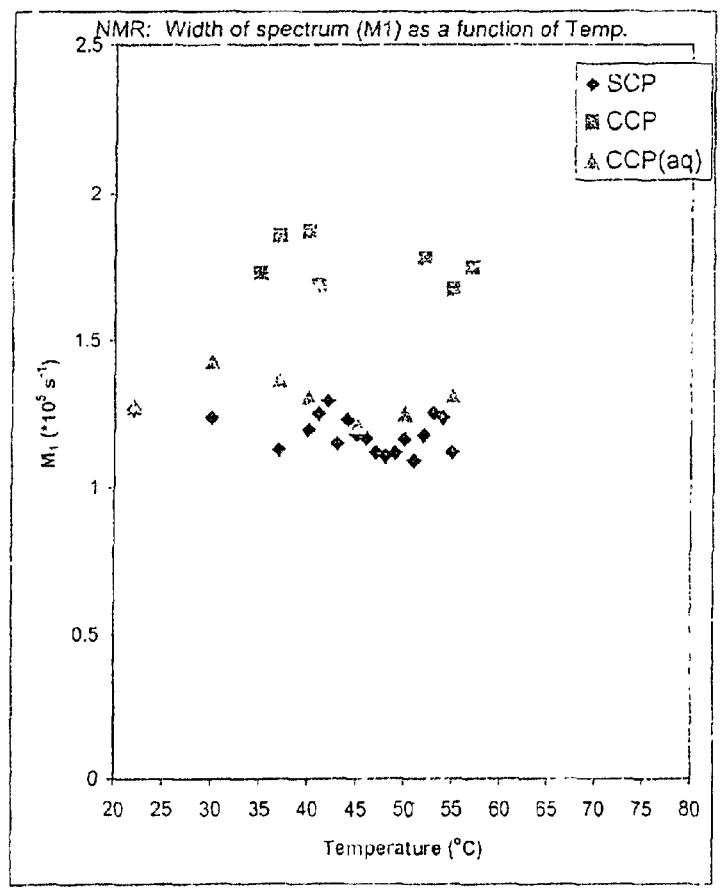
FIG. 2: M1 of three lipid formulations across a wide physiological temperature range.

The results of the first moment measurement by NMR are set out in FIG. 2. NMR spectra of CCP applied to filters show clearly that the crystalline phase is present, as evidenced by a Pake doublet of quadrupolar splitting 126 kHz, which is characteristic of motionless lipid. NMR spectra of CCP in aqueous dispersion, before application to the filters, show no evidence of this large quadrupolar splitting. In fact, the aqueous dispersion of CCP and the SCP on filters give very similar NMR results, all within the liquid crystal range.

Example 3

In this example, the lipid/membrane model of Example 1 is compared directly to untreated pig-skin.

Figure 3:
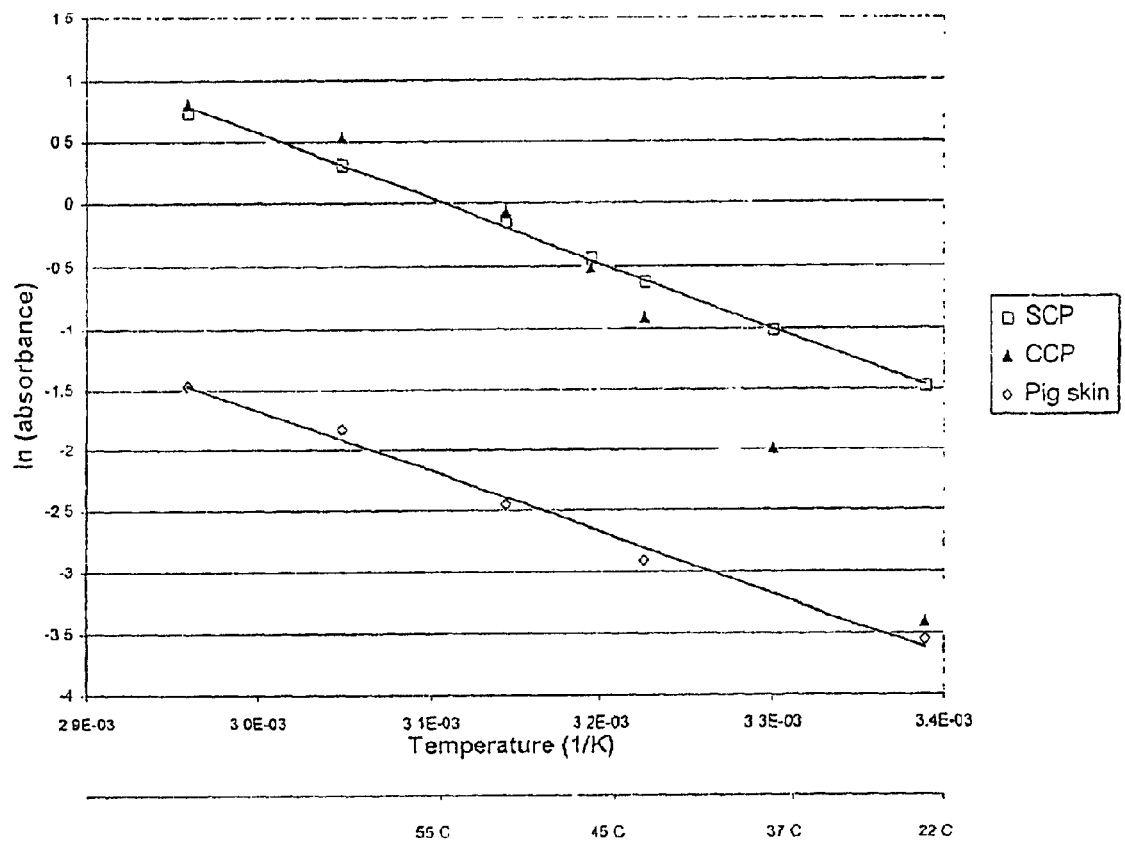
FIG. 3: Water flux across model membranes and pig-skin.

Skin of the domestic white pig was obtained shortly after death, trimmed and frozen. Subsequently, this tissue was mounted in a Franz diffusion chamber, and water flux measurements made as described above. FIG. 3 illustrates the results.

Surprisingly, the absolute values of water flux in pig skin and the ceramide-containing (CCP) model membrane are identical at room temperature (22° C.) under our experimental conditions and are very comparable to values for pig skin reported by other workers using different methods. This contrasts with the SCP formulation which provides a much less effective water-loss barrier at room temperature. Also surprisingly, as temperature increases, CCP on filters gradually loses its improved water-loss protection ability until it reaches the known phase transition point of 45 C where it is indistinguishable from SCP. This effect is attributed to CCP gradually undergoing a phase transition back to the non-crystalline phase at the higher temperatures. Pig skin will also undergo a phase transition above 65 C (see Golden et al. 1987 Biochemistry, 26:2382–8.), but it is not expected to have one at the temperatures shown.

Additionally, the slopes of the ln(water flux) vs. temperature for pig skin and SCP are strikingly similar and similar to the slope one would expect from the increased vapour pressure of water as a function of temperature. Taken together, these results demonstrate that in contrast to CCP, SCP and pig skin do not undergo structural transitions affecting the mechanism of water permeation at the temperatures studied.

Example 4

This example demonstrates the recovery of a mammalian trans-epidermal permeability barrier by the application to the skin of a composition of the invention.

Liposomal compositions according to the invention are prepared as in Example 1.

Figure 4:
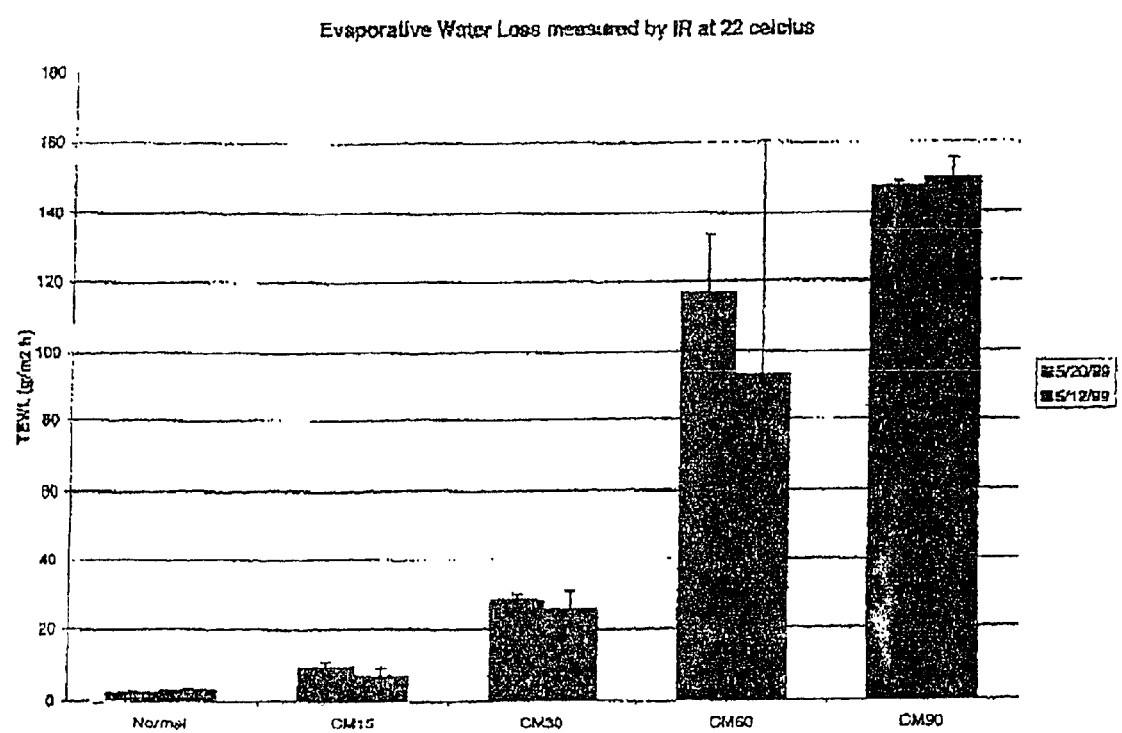
FIG. 4: Standard curve of evaporative Water Loss measured by IR at 22 Celsius for chloroform:methanol treated pig skin.

A sample of pig skin is prepared as in Example 3. However, prior to mounting in the Franz chamber, the skin is treated with excess chloroform: methanol (2:1 v/v) in an Erlenmeyer flask for the indicated time periods. This treatment depletes the intercellular lipids of the skin and provides an accepted model of damaged skin. FIG. 4 is a control experiment showing the effect of time of chloroform treatment on TEWL. Maximum TEWL is observed between 60–90 minutes, indicating the depletion of effectively all intercellular lipids.

Figure 5:
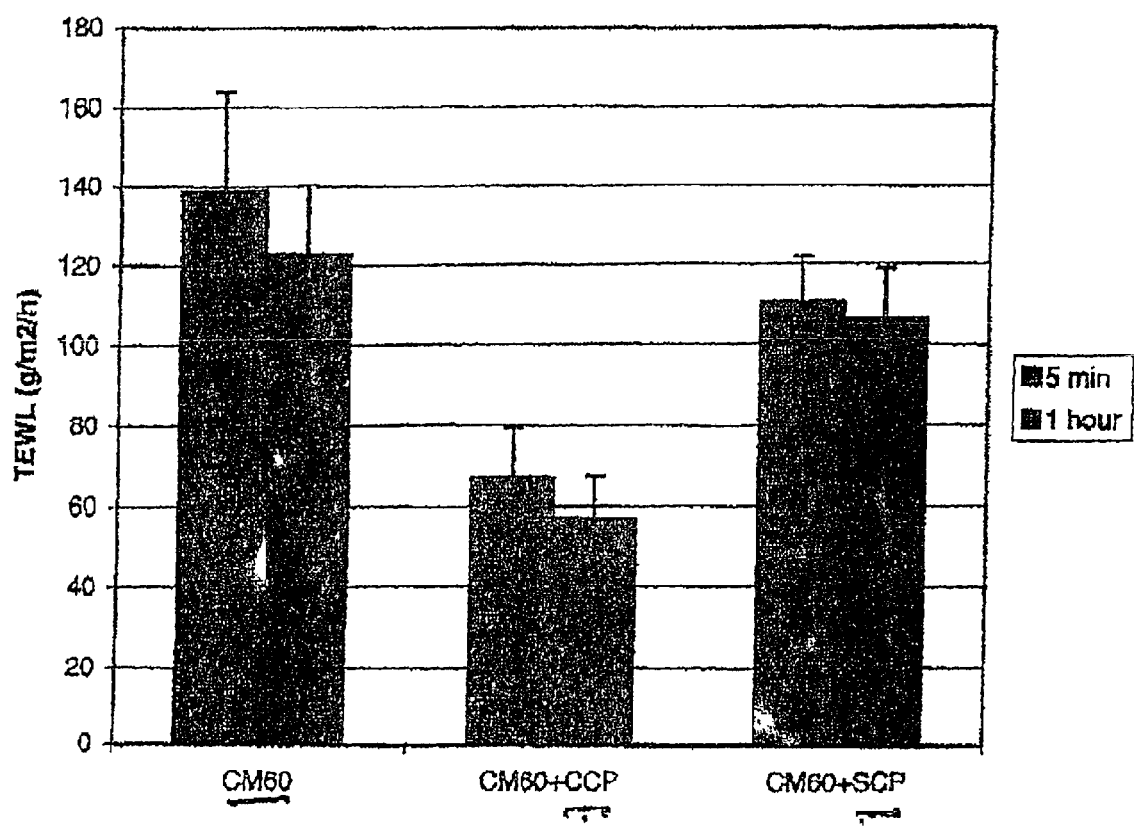
FIG. 5: TEWL of pig R-midsection CM60 samples: untreated; treated with CCP; and treated with SCP. Times indicated are system purging times prior to TEWL analysis.

FIG. 5 demonstrates the recovery of the trans-epidermal permeability barrier using compositions of the invention compared to other compositions. Initially, compositions are liquid-crystal phase liposomes at approximately 8 mg/ml lipid in CHES buffer pH 9.0. The indicated lipid compositions (CCP or SCP) are applied to the skin by pipette. Dosages were the same as those in Example 1, approximately 1 mg lipid per 9 mm diameter section, or about 1.5 mg/cm2. Times indicated are drying times at 40° C., before mounting in the Franz chamber.

Surprising and highly significant differences between the TEWL of the SCP formulation and CCP formulation are found. CCP reduces TEWL by 33% to 50% compared to SCP. These results are attributable to the phase-transition differences of the compositions. The SCP formulation itself shows only a mild improvement over the heavily damaged control skin (CM60).

Example 5

In this example, compositions of the invention are compared to prior art Ah compositions to determine relative effect on TEWL.

Sample 1: Lipids are dissolved independently in organic solvent, then mixed in the following molar ratio: cholesterol; ceramide; linoleic acid: palmitic acid (3:1:1:1). (Prior art formulation) Sample 1 is freeze dried, then reconstituted in a mixture of propylene glycol and ethanol 7:3 (v/v). The concentration of the lipids is 1.2% by weight.

Sample 2: Lipids are dissolved independently in organic solvent, then mixed in the following molar ratio: bovine brain ceramide: cholesterol and palmitic acid (1:1:1) (CCP). Sample 2 is freeze dried, then reconstituted as in Example 1, by hydrating the lyophilized mixture at 95° C. with $10^{-3}$ M CHES buffer, pH 9.

The final lipid concentration of Samples 1 and 2 is 8 mg/ml.

For each sample, five aliquots totalling 1 mg lipid are deposited onto a 9 mm diameter circle of pig skin CM60, prepared as in Example 4. Experiments are conducted as in Example 4.

Results demonstrate that a composition of the invention, CCP demonstrates a 20–75% reduction in TEWL compared to prior art formulation.

What is claimed is:

1. A skin barrier replacement composition comprising an aqueous formulation of at least three lipids in a non-crystalline phase lamellar array which adopt a crystalline lamellar phase upon application to mammalian skin, wherein the at least three lipids comprise a ceramide, a saturated fatty acid and cholesterol and wherein the composition comprises bovine brain ceramide as the ceramide, palmitic acid as the saturated fatty acid and cholesterol in ratios by mol of from 1–5:1–5:1–5, respectively.

2. A skin barrier replacement composition comprising an aqueous formulation of at least three lipids in a non-crystalline phase lamellar array which adopt a crystalline lamellar phase upon application to mammalian skin, wherein the at least three lipids comprise a ceramide, a saturated fatty acid and cholesterol and wherein the composition comprises ceramide 2 as the ceramide, palmitic acid as the saturated fatty acid and cholesterol in ratios by mol of from 1–5:1–5:1–5, respectively.

3. A skin barrier replacement composition comprising an aqueous formulation of at least three lipids in a non-crystalline phase lamellar array which adopt a crystalline lamellar phase upon application to mammalian skin, wherein said non-crystalline phase is a gel.

4. A skin barrier replacement composition comprising an aqueous formulation of at least three lipids in a non-crystalline phase lamellar array which adopt a crystalline lamellar phase upon application to mammalian skin, wherein said non-crystalline phase is a complex phase.

5. The composition of claim 4, wherein said complex phase is a combination of phases selected from among gel, liquid crystal and crystalline phases, wherein the crystalline phase does not exceed 30% of the lipids by mass.

6. A skin barrier replacement composition comprising an aqueous formulation of at least three lipids in a non-crystalline phase lamellar array which adopt a crystalline lamellar phase upon application to mammalian skin, wherein said crystalline phase induced upon application to the skin is greater than 70% crystalline as measured by deuterated fatty acid mobility in NMR.

* * * * *

UNITED STATES PATENT AND TRADEMARK OFFICE
CERTIFICATE OF CORRECTION

| | | |
|---|---|---|
| PATENT NO. | : 6,824,785 B1 | Page 1 of 1 |
| APPLICATION NO. | : 09/780060 | |
| DATED | : December 30, 2004 | |
| INVENTOR(S) | : Kitson et al. | |

It is certified that error appears in the above-identified patent and that said Letters Patent is hereby corrected as shown below:

On title page delete Item (74) and insert item (74)
    --Margaret Polson: Oppedahl Patent Law Firm LLC--

Signed and Sealed this

Eighteenth Day of May, 2010

David J. Kappos
*Director of the United States Patent and Trademark Office*